(12) United States Patent
McGarry et al.

(10) Patent No.: US 6,642,046 B1
(45) Date of Patent: Nov. 4, 2003

(54) METHOD AND APPARATUS FOR PERFORMING BIOLOGICAL REACTIONS ON A SUBSTRATE SURFACE

(75) Inventors: Mark W. McGarry, Scottsdale, AZ (US); Peter Kahn, Phoenix, AZ (US); Todd Tuggle, Chandler, AZ (US); George Hawkins, Gilbert, AZ (US)

(73) Assignee: Motorola, Inc., Schaumburg, IL (US)

( * ) Notice: Subject to any disclaimer, the term of this patent is extended or adjusted under 35 U.S.C. 154(b) by 0 days.

(21) Appl. No.: 09/458,534

(22) Filed: Dec. 9, 1999

(51) Int. Cl.$^7$ ................................................ C12M 1/34
(52) U.S. Cl. ............................... 435/287.2; 435/288.4; 435/288.7; 435/305.3
(58) Field of Search .................... 435/387.1, 287.2, 435/288.4, 288.5, 288.7, 305.3, 305.4

(56) References Cited

U.S. PATENT DOCUMENTS

| | | | | |
|---|---|---|---|---|
| 4,734,372 A | * | 3/1988 | Rotman | 422/48 |
| 4,908,319 A | | 3/1990 | Smyczek et al. | 435/285 |
| 4,974,952 A | * | 12/1990 | Focht | 356/246 |
| 5,038,852 A | | 8/1991 | Johnson et al. | 165/12 |
| 5,100,775 A | | 3/1992 | Smyczek et al. | 435/6 |
| 5,143,854 A | | 9/1992 | Pirrung et al. | 436/518 |
| 5,360,741 A | | 11/1994 | Hunnell | 435/290 |
| 5,414,556 A | * | 5/1995 | Focht | 356/246 |
| 5,474,796 A | | 12/1995 | Brennan | 427/2.13 |
| 5,492,806 A | | 2/1996 | Drmanac et al. | 435/5 |
| 5,525,464 A | | 6/1996 | Drmanac et al. | 435/6 |
| 5,541,061 A | | 7/1996 | Fodor et al. | 435/6 |
| 5,545,531 A | | 8/1996 | Rava et al. | 435/6 |
| 5,571,639 A | | 11/1996 | Hubbell et al. | 430/5 |
| 5,578,832 A | | 11/1996 | Trulson et al. | 250/458.1 |
| 5,580,717 A | | 12/1996 | Dower et al. | 435/5 |
| 5,583,043 A | * | 12/1996 | Sakariassen | 422/104 |
| 5,589,136 A | | 12/1996 | Northrup et al. | |
| 5,593,839 A | | 1/1997 | Hubbell et al. | 435/6 |
| 5,599,695 A | | 2/1997 | Pease et al. | 435/91.1 |

(List continued on next page.)

FOREIGN PATENT DOCUMENTS

| | | |
|---|---|---|
| EP | 0 870 541 A2 | 10/1998 |
| EP | 0 870 541 A3 | 10/1998 |
| WO | WO 98/50154 A1 | 11/1998 |
| WO | WO 00/39587 | 7/2000 |
| WO | WO 02/00336 | 1/2002 |

*Primary Examiner*—David Redding
(74) *Attorney, Agent, or Firm*—Dorsey & Whitney LLP; Robin M. Silva

(57) ABSTRACT

The present invention provides methods and apparatus for performing biological reactions on a substrate surface that use a low volume of sample fluid, accommodate substrates as large as or larger than a conventional microscope slide, accommodate a plurality of independent reactions, and accommodate a substrate surface having one or more hydrogel-based microarrays attached thereto. The invention further provides an apparatus that allows introduction of fluids in addition to sample fluid into each reaction chamber via standard pipet tips and associated pipettor apparatus. The invention further an apparatus that increases reaction reproducibility, increases reaction efficiency, and reduces reaction duration.

The preferred embodiment of the invention is configured to accommodate a standard microscope slide substrate having four hydrogel-based microarrays attached thereto and comprises a base plate having a well structure corresponding to each microarray and two fluid ports extending through the base plate into each well structure, a means for temporarily clamping the substrate against the base plate such that the microarrays face into the well structures, a means for sealing the perimeter around each microarray and well structure, and a means for sealing the fluid ports from the environment.

67 Claims, 11 Drawing Sheets

U.S. PATENT DOCUMENTS

| | | | |
|---|---|---|---|
| 5,631,734 A | 5/1997 | Stern et al. | 356/317 |
| 5,695,940 A | 12/1997 | Drmanac et al. | 435/6 |
| 5,733,729 A | 3/1998 | Lipshutz et al. | 435/6 |
| 5,741,463 A * | 4/1998 | Sanadi | 422/101 |
| 5,744,305 A | 4/1998 | Fodor et al. | 435/6 |
| 5,770,456 A | 6/1998 | Holmes | 436/518 |
| 5,834,758 A | 11/1998 | Trulson et al. | 250/201.2 |
| 5,837,832 A | 11/1998 | Chee et al. | 536/22.1 |
| 5,843,655 A | 12/1998 | McGall | 435/6 |
| 5,847,105 A | 12/1998 | Baldeschwieler et al. | 536/25.3 |
| 5,856,101 A | 1/1999 | Hubbell et al. | 435/6 |
| 5,856,174 A | 1/1999 | Lipshutz et al. | 435/286.5 |
| 5,861,242 A | 1/1999 | Chee et al. | 435/5 |
| 5,874,219 A | 2/1999 | Rava et al. | 435/6 |
| 5,882,930 A | 3/1999 | Baier | 436/49 |
| 5,885,837 A * | 3/1999 | Winkler et al. | 435/287.2 |
| 5,922,591 A | 7/1999 | Anderson et al. | 435/287.2 |
| 5,939,312 A | 8/1999 | Baier et al. | |
| 5,945,334 A | 8/1999 | Besemer et al. | 435/287.2 |
| 5,948,673 A | 9/1999 | Cottingham | 435/287.2 |
| 5,955,283 A | 9/1999 | Bandman et al. | 436/6 |
| 5,955,284 A | 9/1999 | Braxton et al. | |
| 6,258,593 B1 | 7/2001 | Schembri et al. | |
| 6,307,042 B1 | 10/2001 | Goldberg et al. | |
| 6,309,601 B1 | 10/2001 | Juncosa et al. | |
| 6,309,602 B1 | 10/2001 | Ackley et al. | |
| 6,309,889 B1 * | 10/2001 | Cutler et al. | 422/102 |
| 6,315,953 B1 | 11/2001 | Ackley et al. | |
| 6,319,472 B1 | 11/2001 | Ackley et al. | |
| 6,331,274 B1 | 12/2001 | Ackley et al. | |
| 6,375,899 B1 | 4/2002 | Ackley et al. | |
| 6,379,897 B1 | 4/2002 | Weidenhammer et al. | |
| 6,385,080 B1 | 5/2002 | Heller et al. | |
| 6,391,559 B1 * | 5/2002 | Brown et al. | 422/50 |
| 6,395,493 B1 | 5/2002 | Sosnowski et al. | |
| 6,429,027 B1 | 8/2002 | Chee et al. | |
| 2001/0036672 A1 | 11/2001 | Anderson et al. | |
| 2002/0022261 A1 | 2/2002 | Anderson et al. | |
| 2002/0058331 A1 | 5/2002 | Besemer et al. | |
| 2002/0164235 A1 | 11/2002 | Norris et al. | |
| 2002/0174884 A1 | 11/2002 | Certa et al. | |
| 2002/0185610 A1 | 12/2002 | Stern | |
| 2003/0003499 A1 | 1/2003 | Besemer et al. | |
| 2003/0017081 A1 | 1/2003 | Trulson et al. | |

* cited by examiner

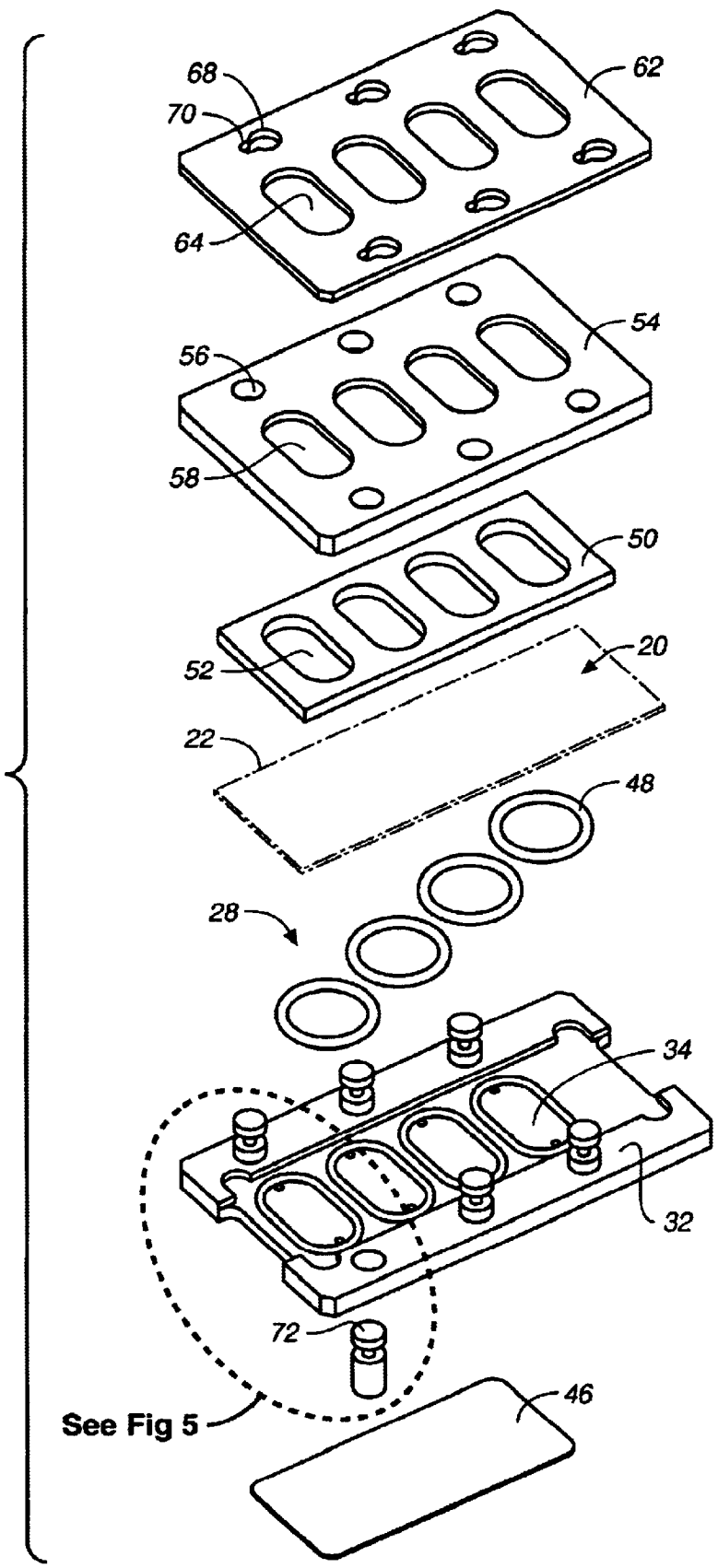
FIG._1

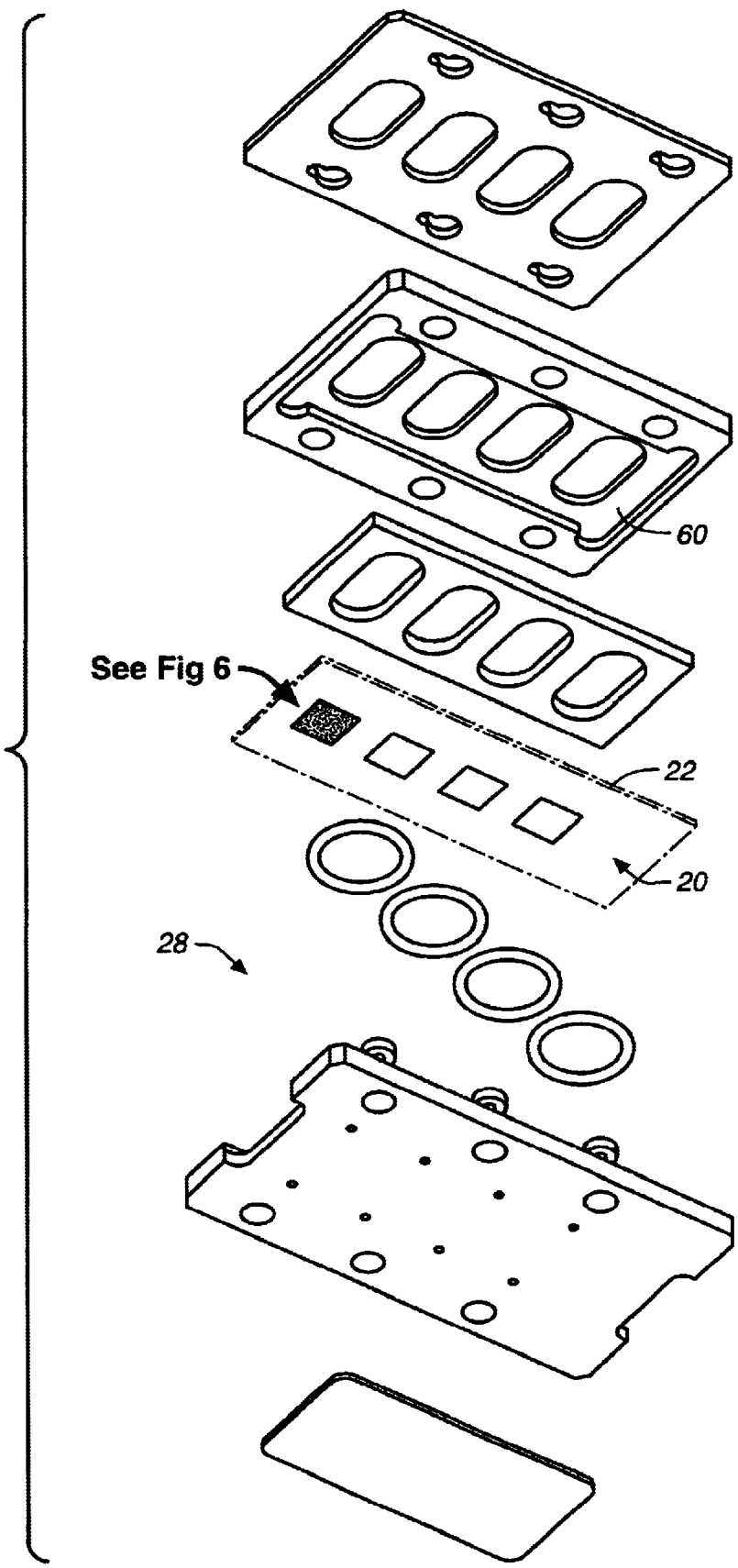
FIG._2

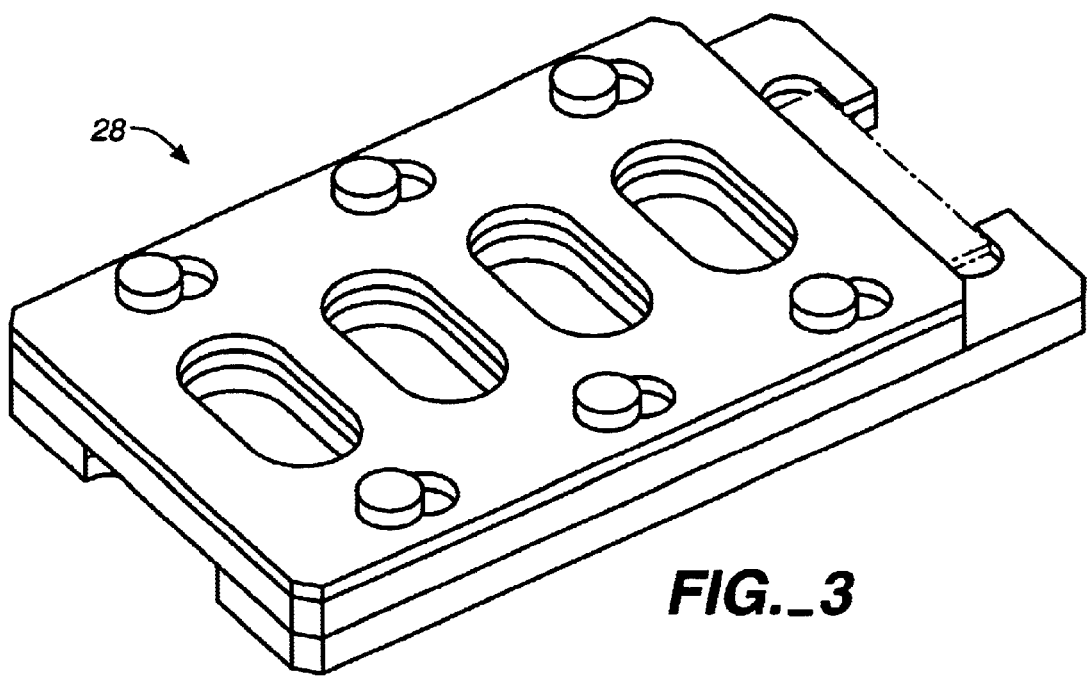
FIG._3
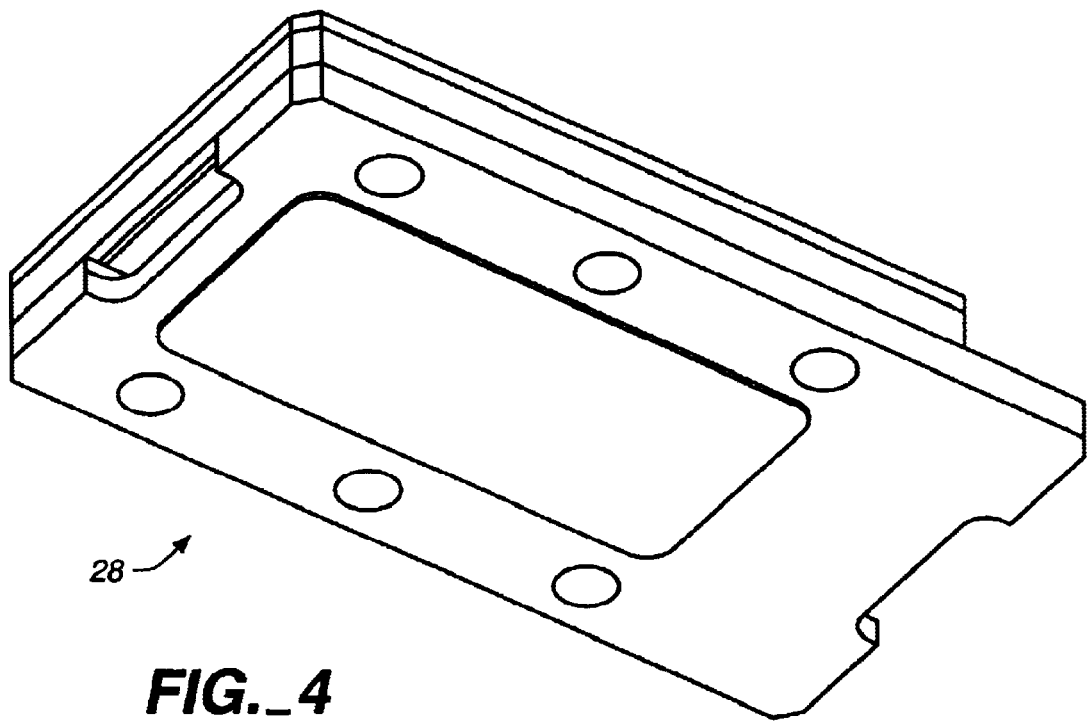
FIG._4

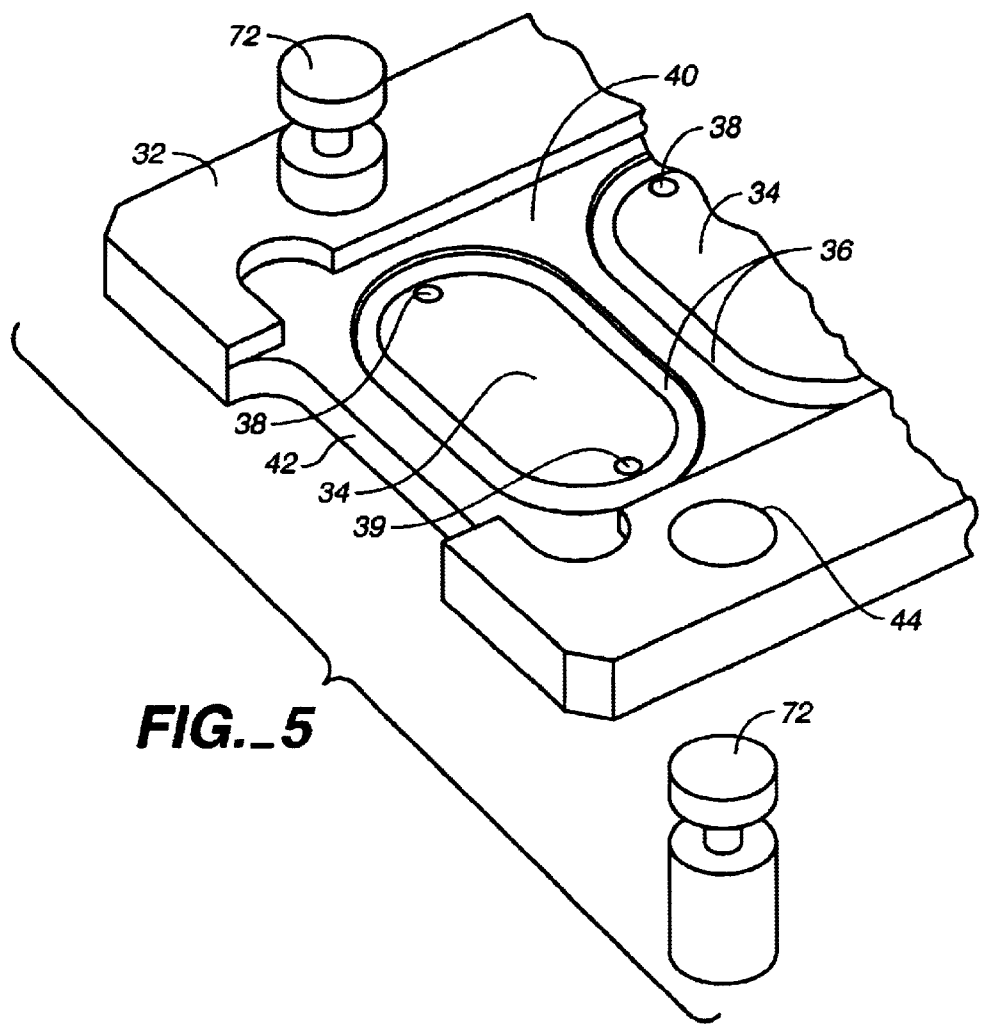
FIG._5
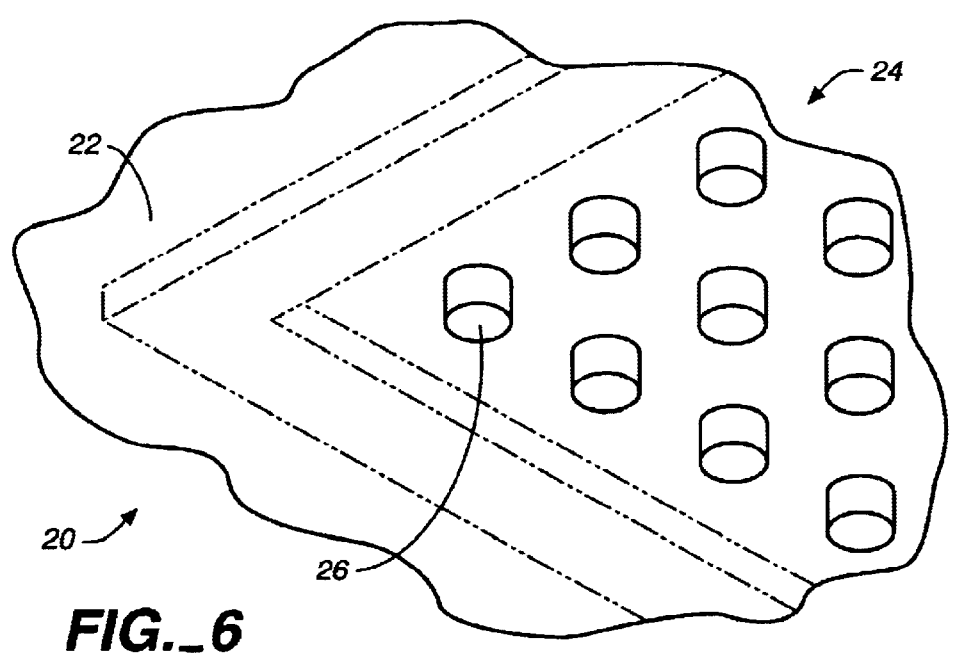
FIG._6

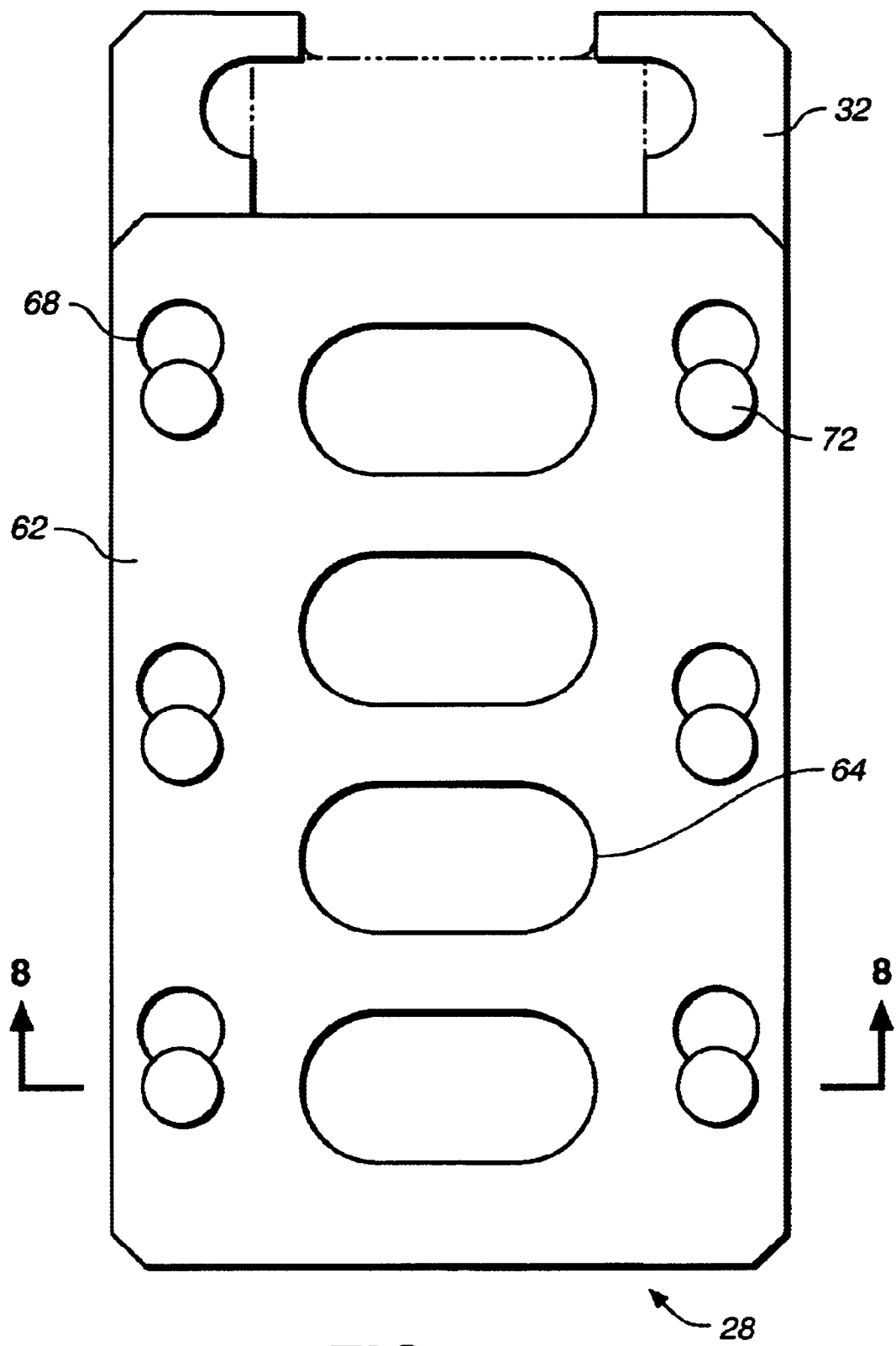
FIG._7

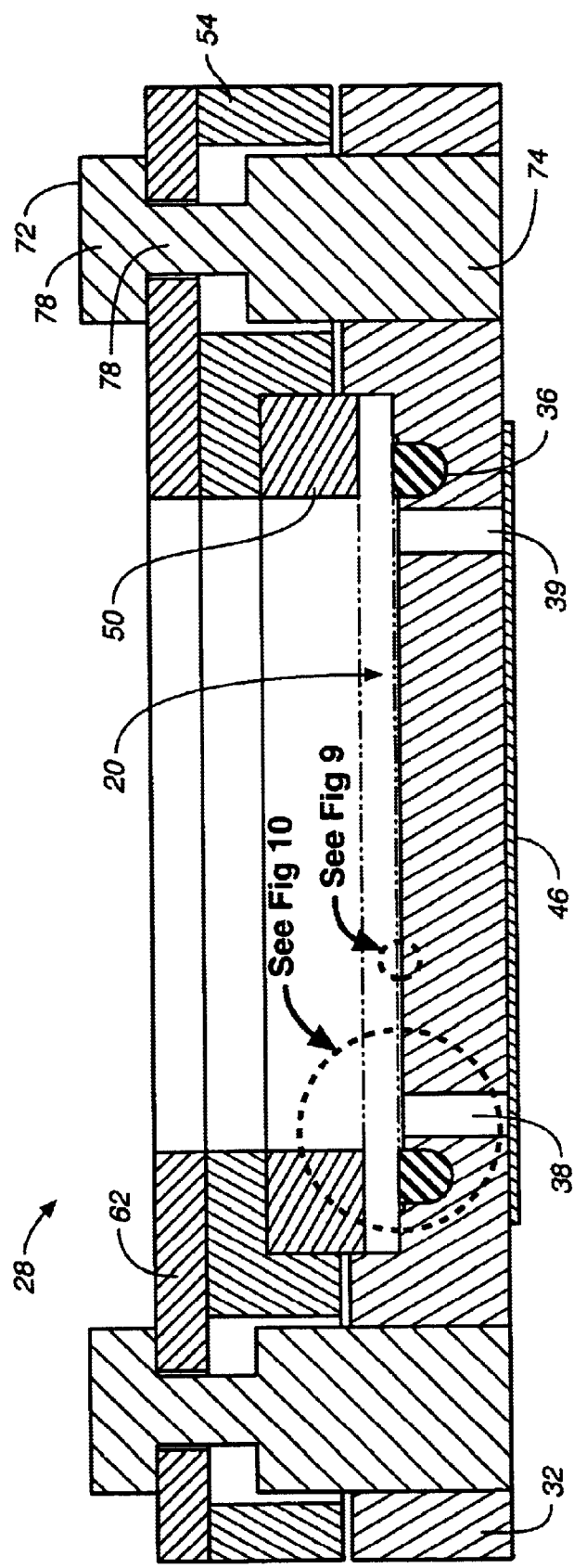
FIG._8

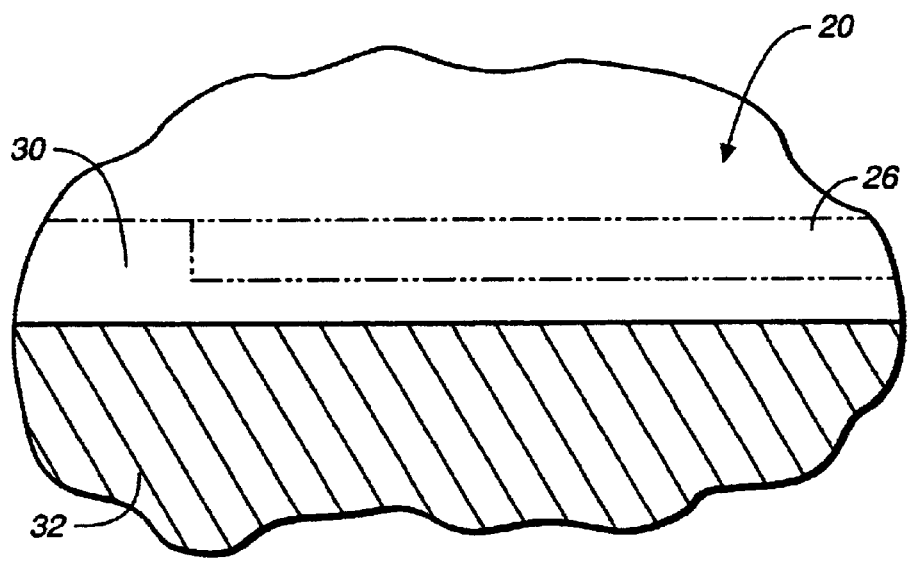
FIG._9
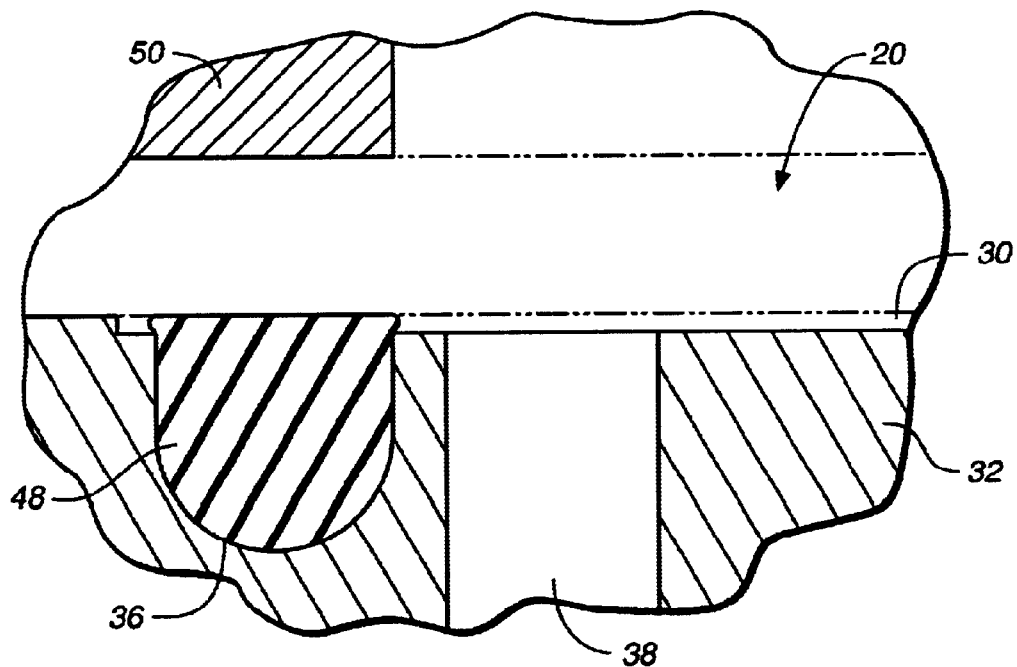
FIG._10

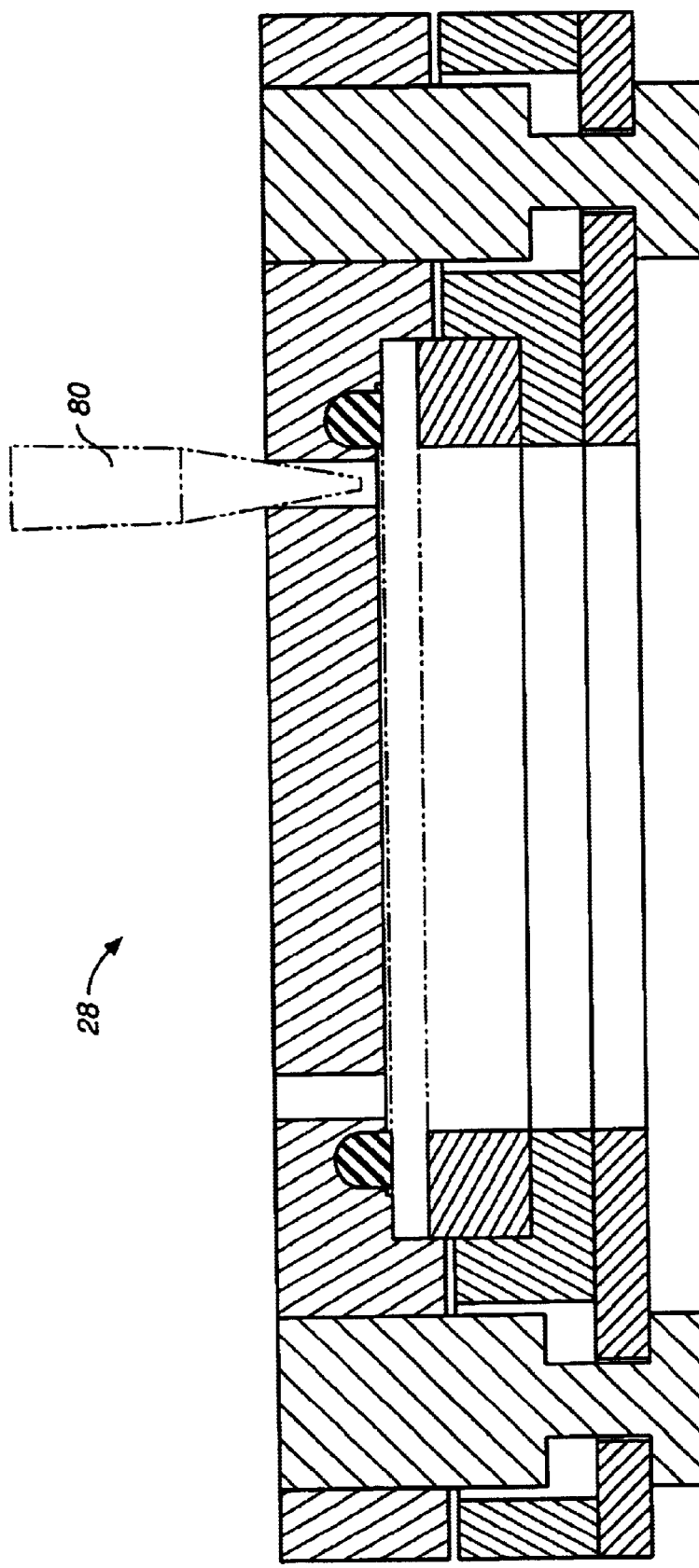
FIG._11

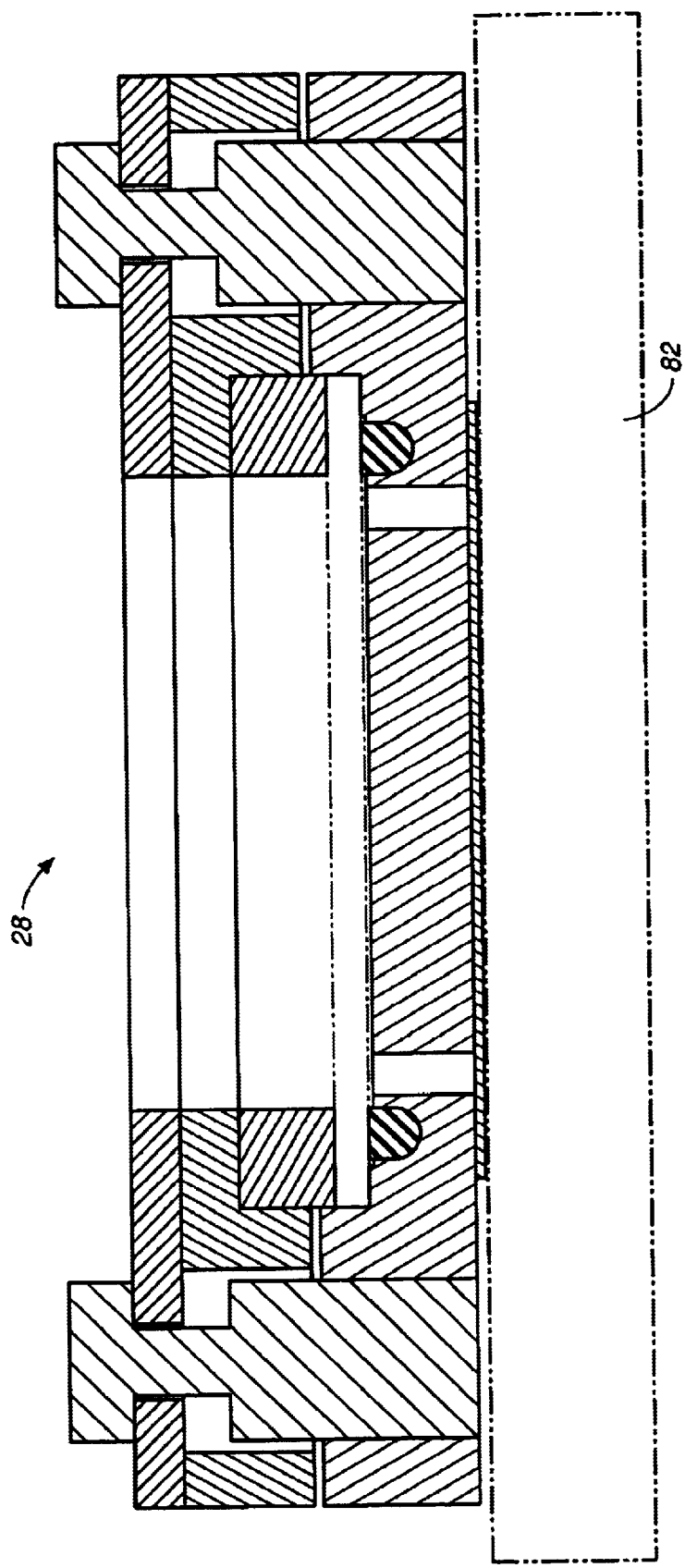

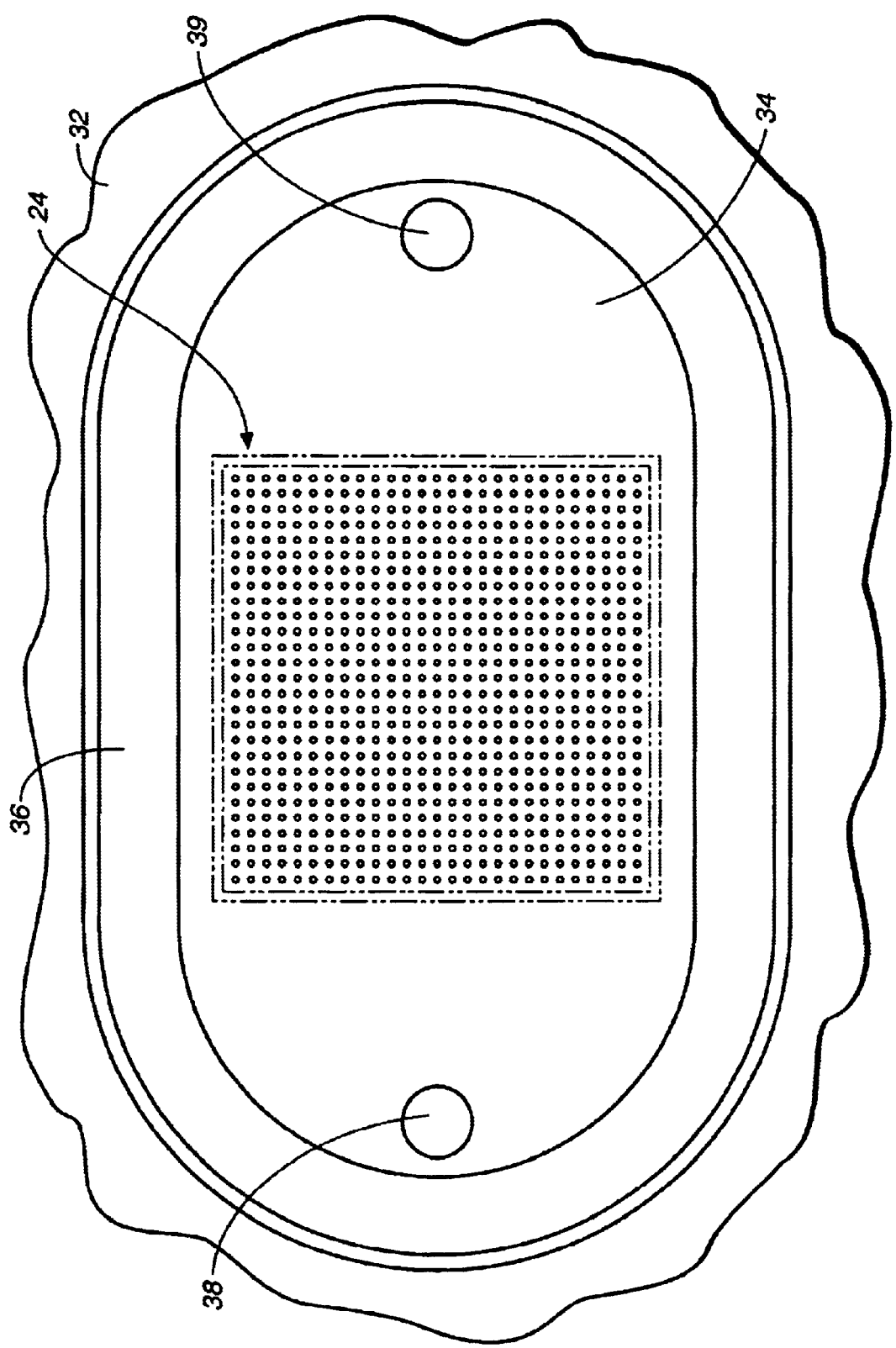
FIG._13

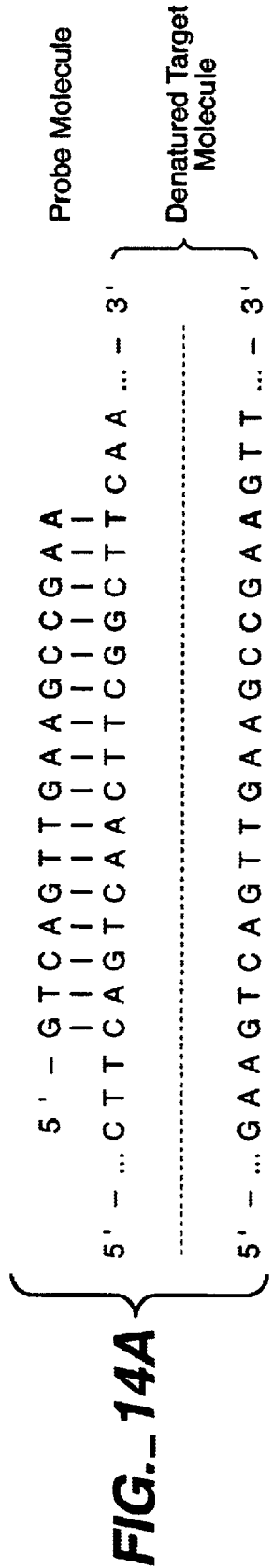
FIG._14A
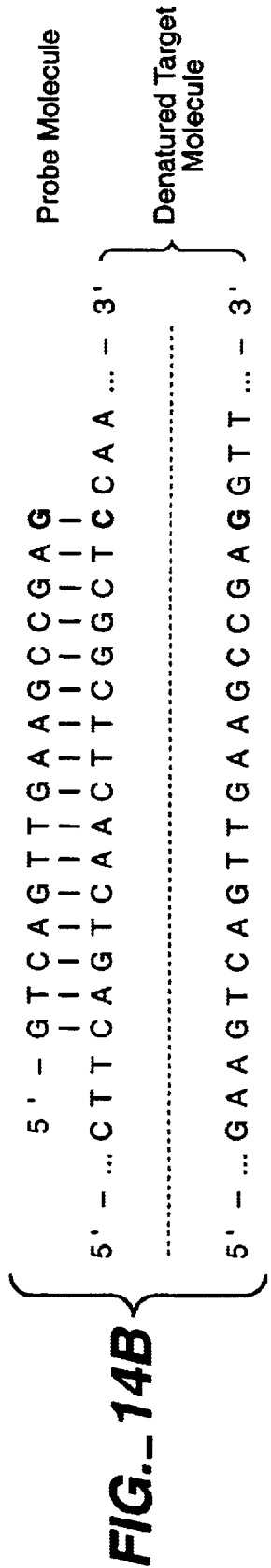
FIG._14B
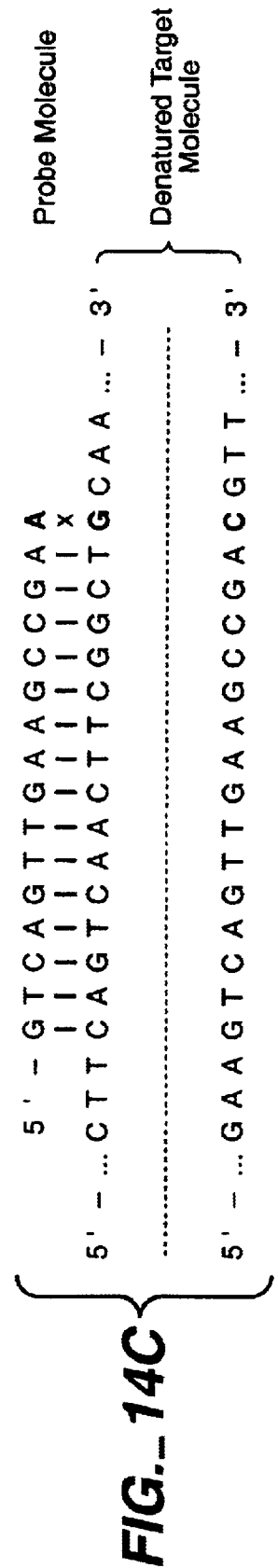
FIG._14C

METHOD AND APPARATUS FOR PERFORMING BIOLOGICAL REACTIONS ON A SUBSTRATE SURFACE

BACKGROUND OF THE INVENTION

1. Field of the Invention

The invention relates to methods and apparatus for performing biological reactions on a substrate surface. More specifically, the invention relates to methods and apparatus for performing thermally controlled biological reactions on a substrate surface having one or more arrays of biologically reactive sites attached thereon. In particular, the invention provides a reusable and thermally controllable reaction apparatus having one or more biologically inert reaction chambers into which biologically reactive sample fluid mixtures are introduced for reaction on a substrate surface having one or more arrays of biologically reactive sites attached thereon.

2. Description of the Prior Art

As research into gene expression and nucleic acid sequencing has progressed in recent years, the need has arisen for high-capacity assaying methods and equipment. Much of the progress in the fields of nucleic acid sequencing and gene expression has resulted from the use of nucleic acid hybridization techniques and antigen/antibody binding techniques, respectively. Assays utilizing specific binding pairs such as complementary nucleic acids including DNA/DNA, DNA/RNA, and RNA/RNA hybrids or antigen/antibody are widely used in the art. The art also discloses various techniques for nucleic acid sequencing based on complementary binding and differential hybridization. Techniques for manufacturing and utilizing microfluidic apparatus for conducting such thermally controlled biological reactions are also well known.

Recent technology utilizes the binding of molecules contained within a biologically reactive sample fluid, hereinafter referred to as target molecules, onto molecules contained within biologically reactive sites, hereinafter referred to as probe molecules. The primary enabler of this technology is a apparatus commonly referred to as a biochip, which comprises one or more 2-dimensional microscopic arrays of biologically reactive sites immobilized on the surface of a substrate. A biologically reactive site is created by dispensing a small volume of biologically reactive fluid onto a discrete location on the surface of a substrate, also commonly referred to as spotting. To enhance immobilization of probe molecules, many biochips include a 2-dimensional array of 3-dimensional polymeric anchoring structures (for example, polyacrylamide gel pads) attached to the surface of the substrate. Probe molecules such as oligonucleotides covalently attach to polyacrylamide-anchoring structures by forming an amide, ester or disulfide bond between the biomolecule and a derivatized polymer comprising the cognate chemical group. Covalent attachment of probe molecules to the polymeric anchoring structure is usually performed after polymerization and chemical cross-linking of the polymer to the substrate is completed.

Existing apparatus for performing thermally-controlled biological reactions on a substrate surface are deficient in that they either require unacceptably large volumes of sample fluid to operate properly, cannot accommodate substrates as large as or larger than a conventional microscope slide, cannot independently accommodate a plurality of independent reactions, or cannot accommodate a substrate containing hydrogel-based microarrays. Most existing apparatus also do not allow introduction of fluids in addition to the sample fluid such as wash buffers, fluorescent dyes, etc., into the reaction chamber. Disposable apparatus require disassembly and reapplication of a new apparatus to the substrate surface every time a new fluid must be introduced. Other existing apparatus are difficult to use in a laboratory environment because they cannot be loaded with standard pipet tips and associated pipettor apparatus.

Many existing apparatus also exhibit unacceptable reaction reproducibility, efficiency, and duration. Reaction reproducibility may be adversely affected by bubble formation in the reaction chamber or by the use of biologically incompatible materials for the reaction chamber. Reaction duration and efficiency may be adversely affected by the presence of concentration gradients in the reaction chamber.

Bubbles can form on introduction of sample fluid to the reaction chamber, at elevated temperatures during the reaction due to the potential high gas content of the fluid, or by outgassing of the reaction chamber materials. When gas bubbles extend over the substrate surface in an area containing biologically reactive sites, the intended reaction may intermittently fail or yield erroneous results because the intended concentration of the sample fluid mixture has been compromised by the presence of gas bubbles. To aggravate the problem, gas bubbles in the reaction chamber attempt to expand at elevated temperatures during the reaction and periodically cause the seal between the substrate surface and reaction chamber apparatus to fail, allowing leakage and evaporation of the sample fluid.

Biologically incompatible reaction chamber materials may cause unacceptable reaction reproducibility, by interacting with the sample fluid, thus causing the intended reaction to intermittently fail or yield erroneous results.

Incomplete mixing of the sample fluid can introduce concentration gradients within the sample fluid that adversely impact reaction efficiency and duration. This effect is most pronounced when there is depletion of target molecules in the local volume surrounding a biologically reactive site. During a biological reaction, the probability that a particular target molecule will bind to a complementary (immobilized) probe molecule is determined by the given concentration of target molecules present within the sample fluid volume, the diffusion rate of the target molecule through the reaction chamber, and the statistics of interaction between the target molecule and the complementary probe molecule. For diagnostic assays, target DNA molecules are often obtained in minute (<picomol) quantities. In practice, it can take tens of hours for a hybridization reaction to be substantially complete at the low target nucleic acid molecule levels available for biological samples. Concentration gradients further exacerbate this problem.

U.S. Pat. No. 5,948,673 to Cottingham discloses a self-contained multi-chamber reactor for performing both DNA amplification and DNA probe assay in a sealed unit wherein some reactants are provided by coating the walls of the chambers and other reactants are introduced into the chambers prior to starting the reaction in order to eliminate flow into and out of the chamber. Unfortunately, no provisions are made for pressurization or mixing of the sample fluid introduced to the chambers, and the apparatus cannot accommodate substrates including microscope slides.

There remains a need in the art for methods and apparatus for performing biological reactions on a substrate surface that use a low volume of sample fluid, accommodate substrates as large as or larger than a conventional microscope slide, accommodate a plurality of independent reactions, and accommodate a substrate surface having one or more hydrogel-based microarrays attached thereto. There also remains a need in the art for an apparatus that allows introduction of fluids in addition to sample fluid into each reaction chamber via standard pipet tips and associated pipettor apparatus. There also remains a need in the art for such an apparatus that increases reaction reproducibility, increases reaction efficiency, and reduces reaction duration. These needs are particularly striking in view of the tremendous interest in biochip technology, the investment and substantial financial rewards generated by research into biochip technology, and the variety of products generated by such research.

SUMMARY OF THE INVENTION

The present invention provides methods and apparatus for performing biological reactions on a substrate surface that use a low volume of sample fluid, accommodate substrates as large as or larger than a conventional microscope slide, accommodate a plurality of independent reactions, and accommodate a substrate surface having one or more hydrogel-based microarrays attached thereto. The invention further provides an apparatus that allows introduction of fluids in addition to sample fluid into each reaction chamber via standard pipet tips and associated pipettor apparatus. The invention further provides an apparatus that increases reaction reproducibility, increases reaction efficiency, and reduces reaction duration.

The invention broadly comprises a base plate having a first surface and a cavity disposed in the first surface, wherein the cavity comprises one or more well structures and a biochip comprising one or more microarrays of biologically reactive sites disposed on a first surface can be inserted into the apparatus such that the first surface of the biochip is in direct communication with the well structures and is removably clamped to the base plate using a compression plate. A sealing member is disposed between the first surface of the substrate and the first surface of the base plate in each well structure, thereby defining one or more reaction chambers. Each well structure has at least two fluid ports for introducing fluid samples into and removing, fluid samples from the reaction chambers. The invention further comprises a seal for the fluid ports.

A preferred embodiment of the invention is configured to accommodate a biochip comprising a standard microscope slide having a plurality of hydrogel-based microarrays attached thereto. A further preferred embodiment of the apparatus includes the biochip.

In preferred embodiments of the present invention, the sealing member around the perimeter of each well structure comprises an O-ring or sheet of gasket material.

In further preferred embodiments, the fluid ports allow introduction of fluid sample via a standard pipet tip or tubing. In still further preferred embodiments, the fluid ports allow interface to an external pumping system that provides mixing and pressurization of the fluid in each reaction chamber to provide uniform target molecule concentration and dissolve gas bubbles, respectively.

In preferred embodiments, the fluid port seal comprises a layer of flexible, thermally conductive material on which is disposed a layer of pressure-sensitive adhesive.

In other preferred embodiments of the invention, the biological compatibility of the base plate material is enhanced by the addition of a biologically compatible surface coating to the first surface of the base plate. The adhesion of the surface coating to the first surface of the base plate may be further enhanced by application of a layer of primer on the first surface of the base plate prior to application of the surface coating.

In further preferred embodiments of the invention, the compression plate is removably affixed to the base plate by a plurality retaining pins disposed along the perimeter of the base plate which fit into corresponding locking apertures disposed along the perimeter of the retaining plate. In yet further preferred embodiments, the compression plate comprises a cavity wherein a compliance layer is seated.

In preferred embodiments of the microfluidic reaction apparatus, the retaining plate, compression plate and compliance layer further comprise one or more viewing ports corresponding in position to the reaction chambers for observation of the biological reactions taking place inside the reaction chambers.

The invention is advantageously used for performing thermally controlled biological reactions, and in preferred embodiments comprises a heating element and a thermal cycling device.

Specific preferred embodiments of the present invention will become evident from the following more detailed description of certain preferred embodiments and the claims.

DESCRIPTION OF THE DRAWINGS

FIG. 1 is an exploded perspective view from the upper side of a specific embodiment the present invention, illustrating the relationships between the various components and a biochip.

FIG. 2 is an exploded perspective view from the lower side of the apparatus of FIG. 1, illustrating the proper orientation of a biochip.

FIG. 3 is a perspective view from the upper side of the apparatus of FIG. 1, illustrating the apparatus as assembled and ports for viewing the contents of each reaction chamber.

FIG. 4 is a perspective view from the lower side of the apparatus of FIG. 1, illustrating the relationship of the fluid port-sealing member to the base plate.

FIG. 5 is an enlarged partial view of the apparatus of FIG. 1, illustrating details of the base plate and the relationship of the retaining pins to the base plate.

FIG. 6 is an enlarged partial view of the biochip as shown in FIG. 2, illustrating a hydrogel-based microarray attached to a substrate surface.

FIG. 7 is a top view of the apparatus of FIG. 1, illustrating ports for viewing the contents of each reaction chamber.

FIG. 8 is a cross-sectional view of the apparatus of FIG. 1 taken along line 8—8 in FIG. 7, illustrating a reaction chamber.

FIG. 9 is an enlarged partial view of the apparatus of FIG. 1, illustrating the spatial relationship between a reaction chamber and a biochip.

FIG. 10 is an enlarged partial view of the apparatus of FIG. 1, illustrating a reaction chamber seal.

FIG. 11 is a cross-sectional view of the apparatus of FIG. 1 taken along line 8—8 in FIG. 7, illustrating a pipet tip inserted into a fluid port.

FIG. 12 is a front-end plan view of the apparatus of FIG. 1, illustrating the application of a heating element for temperature cycling.

FIG. 13 is a top view of the apparatus of FIG. 1, illustrating an O-ring groove in relation to a well structure and microarray.

FIGS. 14A–14B and 14C are illustrations of the samples discussed in example 2.

DETAILED DESCRIPTION OF THE PREFERRED EMBODIMENTS

The present invention provides methods and apparatus for performing biological reactions on a substrate layer having a multiplicity of biologically reactive sites disposed thereon. The invention comprises a microfluidic reaction apparatus having one or more individual reaction chambers in direct communication with a biochip, preferably comprising one microarray of oligonucleotide probes, corresponding to each reaction chamber, disposed on the surface of the substrate, wherein each probe is anchored to the substrate by a polyacrylamide gel pad. The apparatus is advantageously used for performing multiple, parallel, thermally controlled biological reactions, most preferably hybridization reactions. Use of the reaction apparatus of the present invention, however, is not limited to DNA hybridization or thermally-controlled biological reactions. Those skilled in the art will recognize various additional uses for the apparatus. For example, the amplification of nucleic acids or the addition of labels to nucleic acids generally results in the presence of various unwanted components in the sample fluid, e.g., unincorporated nucleotides, enzymes, or DNA molecules that are of no interest. With this apparatus, probes can be used to capture nucleic acids of interest and allow the reaction by-products to be washed out of the reactor.

The preferred embodiments of the present invention and its advantages over previously investigated apparatus are best understood by reference to FIGS. 1–13 and Examples 1–2.

As used herein, the term "biochip" refers to one or more microarrays of biologically reactive sites immobilized on the surface of a substrate. Commonly used substrates include soda lime glass sheets and microscope slides.

As used herein, the term "microarray" refers to an addressable 2-dimensional microscopic spatial arrangement, particularly an arrangement of biologically reactive sites.

As used herein, the terms "biomolecular probe" and "oligonucleotide probe" refer to a nucleic acid sequence used to detect the presence of a complementary target sequence by hybridization with the target sequence.

As used herein, the term "standard pipet tip" refers to any commonly used commercially available pipet tip, including but not limited to the "Yellow Tip" 1-200 microliter tip and the "Blue Tip" 100-1000 microliter tip.

As used herein, the term "thermal cycling" refers to the process of rapidly and repeatedly increasing and decreasing temperature in a cyclic fashion, specifically the temperature of a reaction chamber.

FIG. 1 is an exploded perspective view from the upper side of a preferred embodiment of the present invention, illustrating the relationships between the various components. In this embodiment, the apparatus comprises a base plate 32 having a first surface, a second surface, a first cavity 40 comprising four well structures 34 disposed in the first surface. A biochip 20 having a first surface containing a plurality of biologically reactive sites is inserted in the apparatus such that the biochip is removably seated in the first cavity 40 and the first surface of the biochip is in direct communication with one or more well structures 34. Each well structure 34 includes a groove 36 for setting an O-ring 48 between the biochip 20 and the base plate 32, wherein the O-ring 48 defines a reaction chamber 30 between the biochip 20 and the base plate 32. A first fluid port 38 and a second fluid port 39 extend through base plate 32 into each well structure 34. A port seal 46 can be removable applied to the second surface of base plate 32 to temporarily close fluid ports 38 and 39, thereby isolating contents of reaction chamber 30 from the environment.

Biochip 20 comprises one or more microarrays 24 of biologically reactive sites 26 disposed on a first surface of the substrate 22 facing a first surface of the base plate 32. A compliance layer 50 is permanently affixed in a cavity 60 in compression plate 54, and the compression plate 54 is then removably seated on base plate 32, thereby removably locking substrate 22 into base plate cavity 40.

The assembly is locked together with retaining plate 62 and retaining pins 72, having a body 74, a neck 76, and a head 78. The body 74 of each retaining pin 72 is press fit into a pin aperture 44 disposed along the perimeter of base plate 32. Retaining pin body 74 extends through a corresponding pin aperture 56 in compression plate 54. The neck 76 and head 78 of retaining pin 72 extend through a corresponding pin aperture 66 in retaining plate 62. The retaining pin aperture 66 in retaining plate 62 comprises a substantially circular main section 68 configured to accept the diameter of pin head 78, and a notch 70 extending from the main section 68 configured to accept the diameter of pin neck 76, but smaller than the diameter of pin head 78.

FIG. 2 is an exploded perspective view from the lower side of reaction apparatus 28, illustrating the orientation of biochip 20 in relation to base plate 32. FIG. 3 is a perspective view from the upper side of apparatus 28, illustrating apparatus 28 as assembled. FIG. 4 is a perspective view from the lower side of apparatus 28, illustrating the relationship of sealing member 46 to base plate 32.

FIG. 5 is an enlarged partial view of apparatus 28, illustrating details of base plate 32 and the relationship of retaining pins 72 to base plate 32. Base plate 32 is most preferably 5 millimeters thick, 44 millimeters wide, and 82 millimeters long, and comprises two notches 42, six pin apertures 44, first cavity 40, and well structures 34, each having an O-ring groove 36, and first and second fluid ports 38 and 39. The base plate material is preferably thermally conductive in order to conduct heat from heating element 82 to the fluid inside each reaction chamber 30. The conductivity of the base plate material is most preferably selected to provide for alteration of the fluid temperature by at least 2 degrees centigrade per second over a range from zero degrees centigrade to 100 degrees centigrade. The base plate material is preferably titanium, copper, aluminum, ceramic, or any other material having similar mechanical and thermal properties that will not introduce gas bubbles into the reaction chamber by outgassing, and most preferably is grade 2 commercially pure titanium.

Optional base plate notch 42 is located on either end of base plate 32 as shown in FIG. 1, 2, 4, and 5. Notch 42 is configured to allow laboratory technicians to easily remove a biochip 20 with their fingers, and is most preferably 20 millimeters wide and extends laterally most preferably 4 millimeters into base plate 32.

Base plate second cavity 41 is most preferably 25 millimeters wide, 75 millimeters long, and 1 millimeter deep. Each dimension of cavity 41 is slightly larger than the corresponding size of biochip 20 to ensure minimum play of biochip 20. In an alternative configuration, biochip 20 is permanently affixed to the base plate 32, thus forming a single integrated component.

Each pin aperture 44 is disposed along the perimeter of base plate 32 as shown in FIG. 7 and extends entirely through base plate 32. The pin aperture 44 is preferably circular, having a diameter of most preferably 5 millimeters, and allows heavy press-fit around body 74 of retaining pin 72.

The depth of each well structure 34 is preferably between 25 micrometers and 150 micrometers, more preferably between 75 micrometers and 150 micrometers, and most preferably between 100 micrometers and 150 micrometers. The depth selected is critical for developing the capillary action required to avoid gas bubble formation upon introduction of fluid into each reaction chamber 30. It is also critical to minimize the depth of well structure 34 in order to correspondingly reduce the volume of fluid required to fill reaction chamber 30. The volume of reaction chamber 30 is most preferably 33 microliters when well structure 34 is 125 micrometers deep and ports 38 and 39 are each 1.4 millimeters in diameter.

As shown in FIG. 13, each O-ring groove 36 is configured so that a seated O-ring 48 completely surrounds one microarray 24 of biologically reactive sites 26 on biochip 20. As shown in FIG. 10, each O-ring groove 36 preferably comprises an oblong channel that extends most preferably 1.6 millimeters into base plate 32 relative to the first surface of base plate 32. Groove 36 has circular end portions most preferably 11.5 millimeters in diameter, measured from the center of groove 36 to the inner perimeter of the groove, and most preferably 9.5 millimeters apart from center-to-center. The width of the groove, as shown in FIG. 10, is chosen such that it makes a slight interference fit with an O-ring 48, and is most preferably 1.6 millimeters in the embodiment illustrated. This condition reduces the opportunity for trapped gas bubbles to form at the interface surface between each O-ring 48 and O-ring groove 36. Such trapped gas bubbles could expand during heating and cause seal breach. The dimensions of groove 36 are limited only by the size and shape of microarray 24. As shown in FIG. 13, the boundary of each well structure 34 extends slightly outward from the outermost perimeter of O-ring groove 36, allowing room for O-ring 48 to deform during compression of biochip 20 into the surface of second cavity 41, thereby forming a tighter, seal between biochip 20 and base plate 32.

A first fluid port 38 is located in the well structure 34 immediately adjacent to the circular end portion of the inner perimeter of O-ring groove 36 as shown in FIG. 13. A second fluid port 39 is located in the well structure 34 immediately adjacent to the opposite circular end portion of the inner perimeter of O-ring groove 36. The circular end portions of each O-ring groove 36 provide a gradual change in flow geometry which considerably reduces the potential for bubble formation during introduction of a fluid though fluid port 38 and removal through fluid port 39. End portions that are parabolic or triangular in profile, or any shape that provides a gradual change in flow geometry, could also be used to create the same effect.

Each fluid port 38 and 39 is intended for interfacing to pipet tip 80 as shown in FIG. 11 and has a diameter preferably between 0.25 millimeters and 1.5 millimeters, more preferably between 0.75 millimeters and 1.5 millimeters, and most preferably between 1.25 millimeters and 1.5 millimeters. Pipet tip 82 is preferably disposable and made of polypropylene, and can interface with a standard pipettor for manual loading of the reaction chambers. Many other similar types of pipet tips are commonly available and would be useful in the present invention.

A biologically compatible outer surface coating is optionally applied to base plate 32 and retaining pins 72 after all retaining pins 72 are press-fitted into each pin aperture 44 of base plate 32. To enhance adhesion performance of the outer surface layer to base plate 32, a layer of biologically compatible primer is optionally first applied to base plate 32. Preferably the surface coating is selected from fluorinated ethylene propylene (commonly known under the trademark Teflon®), gold, platinum, polypropylene, an inert metal oxide, or any material having similar biological compatibility and mechanical properties. Most preferably, the surface coating is Teflon®. The primer material is preferably Xylan®, Teflon®, polypropylene, an inert metal oxide, or any material having similar biological compatibility and mechanical properties.

Each O-ring 48 preferably has a circular cross-section of most preferably 1.8 millimeters in diameter, and a circular profile the inside diameter of which is most preferably 14 millimeters. Preferably the O-ring material is selected from nitrile, silicone, Kalrez®, or any biologically inert material having similar size and mechanical properties, that will not introduce gas bubbles into the reaction chamber due to outgassing. Most preferably, the O-ring is made of nitrile. As shown in FIG. 10, each O-ring 48 fits into a corresponding O-ring groove 36 in base plate 32 such that no air gaps form between O-ring 48 and O-ring groove 36. When reaction chamber apparatus 28 is assembled correctly, each well structure 34 allows deformation of a corresponding O-ring 48 as shown in FIG. 10.

Biochip 20 broadly comprises substrate 22 and one or a plurality of microarrays 24 disposed on a first surface thereof. In a preferred embodiment, biochip 20 includes four microarrays 24. The dimensions of substrate 22 are preferably between 25 millimeters wide by 75 millimeters long by 1 millimeter thick and 325 millimeters long by 325 millimeters wide by 2 millimeters thick. Most preferably, substrate 22 is a standard soda lime glass microscope slide 25 millimeters wide by 75 millimeters long by 1 millimeter thick. Alternative substrate materials include silicon, fused silica, borosilicate, or any rigid and biologically inert glass, plastic, or metal. As shown, biochip 20 must be oriented with the microarray 24 bearing surface facing toward base plate 32. When assembled as shown, four reaction chambers 30 are formed, each defined by a volume bounded by biochip 20, each O-ring 48, and each corresponding well structure 34.

As shown in FIG. 13, in a preferred embodiment, each microarray 24 has twenty seven biologically reactive sites 26 in one direction and twenty seven in a direction normal to the first direction. As shown in FIG. 6, each site 26 contains a biologically reactive three-dimensional polymerized polyacrylamide gel structure 27 affixed to substrate 22. Each gel structure 27 is preferably cylindrical, most preferably having a 113 micron diameter and a 25 micron thickness. The distance between each site 26 within each microarray 24 is most preferably 300 micrometers, and the distance between each microarray 24 is most preferably 15 millimeters. Each microarray 24 is also preferably isolated by a polyacrylamide gel boundary 25. Each site 26 could alternatively comprise biologically reactive reagents attached directly to substrate 22.

Optional compliance member 50 is intended to provide a uniform distribution of clamping pressure over biochip 20 without cracking substrate 22. The general size of compliance member is intended to substantially match the overall size of substrate 22. Compliance member 50 is most preferably 65 millimeters long, 26 millimeter wide, and 3 millimeter thick, and is formed of a layer of pressure-sensitive adhesive disposed on a layer of low-compression material, preferably selected from silicone sponge rubber, natural sponge rubber, neoprene sponge rubber, or any material having similar mechanical properties. Compliance member 50 further preferably includes four viewing ports 52, each of which allows visual inspection of a corresponding reaction chamber 30 and corresponds in size and shape to the inner perimeter of each O-ring groove 36 in base plate 32 as shown in FIG. 8. The adhesive layer permanently attaches compliance member 50 to cavity 60 of compression plate 54 as shown in FIG. 8.

Compression plate 54 is most preferably 44 millimeters wide, 69 millimeters long, and 4 millimeters thick. Compression plate 54 is preferably formed of fluorinated ethylene propylene, acetal resin, polyurethane, polypropylene, acrylonitrile-butadiene-styrene (ABS), or any material having similar mechanical properties, and is most preferably formed of Teflon. Compression plate 54 further preferably includes six retaining pin apertures 56, four viewing ports 58, and cavity 60. Retaining pin apertures 56 corresponding to the six retaining pins 72 in base plate 32 are located around the periphery of compression plate 54 and pass entirely through compression plate 54 and as shown in FIG. 1. The pin apertures 56 are most preferably 5.5 millimeters in diameter. Each viewing port 58 allows visual inspection of a corresponding reaction chamber 30 and corresponds in size, shape, and location to each corresponding viewing port 52 in compliance member 50 as shown in FIG. 8. Compression plate cavity 60 is most preferably 2.2 millimeters deep, 26 millimeters wide, and 65 millimeters long, and is configured to contain compliance member 50 with minimum play.

Retaining plate 62 is most preferably 44 millimeters wide, 69 millimeters long, 1.5 millimeters thick. The retaining plate 62 is preferably stainless steel, copper, aluminum, titanium, or any material having similar mechanical properties, more preferably is stainless steel, and most preferably is 300 series stainless steel. Retaining plate 62 further preferably comprises four viewing ports 64 located around the periphery of retaining plate 62 and six retaining pin apertures 66, all of which pass entirely through the thickness of retaining plate 62. Each viewing port 64 allows visual inspection of a corresponding reaction chamber 30 and corresponds in size, shape, and location to each corresponding viewing port 58 in compression plate 54. Each retaining aperture 66 further includes a main section 68 that is substantially circular and a notch 70 extending from the main section 68. Each main section 68 is most preferably 5.5 millimeters in diameter, allowing a pin head 78 to pass through. Each notch 70 is most preferably 2.2 millimeters in diameter, having a center 4 millimeters from the center of the corresponding main section 68 as shown in FIG. 1.

As shown in FIG. 8, each retaining pin 72 is generally cylindrical and is formed of stainless steel, aluminum, titanium, ceramic, or any material having similar mechanical properties. More preferably, retaining pin 72 is stainless steel, and most preferably is 300 series stainless steel. Retaining pin 72 preferably comprises body 74, neck 76, and head 78. Body 74 has a circular cross section most preferably 5 millimeters in diameter and is most preferably 7.5 millimeters long. Body 74 is designed specifically to be press-fitted into a pin aperture 44 such that the end of body 74 is flush to the outer surface of base plate 32. Alternatively, retaining pins 72 could be an integral molded portion of base plate 32. Substrate 22 could also be clamped to base plate 32 using standard fasteners including screws in place of retaining pins 72. In large throughput embodiments, an automated clamping mechanism could be used to simultaneously clamp one or more substrates 22 to a base plate 32.

Pin neck 76 has a circular cross-section most preferably 2 millimeters in diameter and 3 millimeters long and is designed specifically to engage notch 70 in the retaining pin aperture 66 of retaining plate 62. Head 78 has a circular cross-section most preferably 5 millimeters in diameter and is most preferably 2 millimeters long.

Port seal 46 is most preferably 52 millimeters long, 24 millimeters wide, 0.1 millimeters thick, and comprises a layer of thermally conductive material having a biologically inert pressure-sensitive adhesive backing attached thereto. The conductivity of port seal 46 is preferably selected to allow alteration of the fluid temperature by heating element 82 at a rate of at least 2 degrees centigrade per second over a range from zero degrees centigrade to 100 degrees centigrade. Most preferably, the thermally conductive material is aluminum foil. After reaction chamber apparatus 28 is assembled and loaded with fluid, port sealing member 46 is temporarily affixed to base plate 32 such that it completely seals off all ports 38 and 39 as shown in FIG. 4.

Heating element 82 heats reaction chamber apparatus 28 by conduction directly through port sealing member 46 and base plate 32, and preferably is capable of altering the temperature of fluid inside each reaction chamber 30 by at least 2 degrees centigrade per second over a range from zero degrees centigrade to 100 degrees centigrade. The embodiment describe herein is intended to interface with a flat block style Alpha Module heating element and a corresponding PTC-220 DNA Engine Tetrad available through MJ Research, Inc. as shown in FIG. 12, although many other types of thermal cycling systems that provide conductive or convective heating could be used.

The preferred embodiment of the reaction apparatus is assembled as follows. Retaining pins 72 are press-fit into base plate pin apertures 44. A layer of primer is then applied to base plate 32 containing retaining pins 72, followed by a layer of biologically compatible surface coating. The substrate is then positioned in base plate cavity 40, with the surface containing the microarrays 24 of biologically reactive sites 26 facing the first surface of the base plate 32. Compliance layer 50 is permanently affixed in compression plate cavity 60 by application of the adhesive layer to the compression plate 54. The pin apertures 56 in compression plate 54 are aligned with the retaining pins 72, and compression plate 54 is then seated on base plate 32. The main sections 68 of retaining pin apertures 66 in retaining plate 62 are aligned with retaining pin heads 78, retaining plate 62 is seated on compression plate 54, and retaining plate 62 is then compressed towards base plate 32 such that pin head 78 extends above retaining plate 62. Retaining plate 62 is shifted laterally such that notch 70 engages each corresponding pin neck 76. Other methods of temporarily locking the compression plate to the base plate, including the use of an external clamp around the base plate and the compression plate or a layer of adhesive between the base plate and the compression plate, could also be used.

The reaction chambers 30 are loaded by inserting pipet tip 82 into first fluid port 38 as far as is necessary to create a seal between tip 82 and port 38, and then slowly introducing fluid into the corresponding reaction chamber 30 using a standard pipettor. Second fluid port 39 allows air to escape as fluid enters reaction chamber 30 through first port 38. Pipet tip 82 is removed from first port 38 when reaction chamber 30 and second fluid port 39 are completely loaded with fluid. If substrate 22 is visually transparent, each reaction chamber 30 may be visually inspected through each compression plate viewing port 58 and retaining plate viewing port 64 immediately after loading for the presence of gas bubbles. If gas bubbles are present over any microarray 24, the fluid loading process must be performed again, or the reaction chamber must be pressurized. Pressurization may be provided manually by inserting additional fluid through a pipet tip inserted into the first fluid port while the second fluid port is sealed, or may be provided automatically by use of a pump and tubing attached to the first fluid port. Preferably the chamber is pressurized to between 27 and 207 kPa (4 and 30 psi), more preferably between 55 ad 69 kPa (8 and 10 psi), and most preferably to about 55 kPa (8 psi). Any other gas bubbles including those away from the edges of any microarray 24, especially those near ports 38 and 39, are harmless and can be ignored. After inspection, port seal 46 is affixed to the lower surface of base plate 32 by applying the pressure-sensitive adhesive side of the port seal port 46.

Once assembled, the reaction chamber apparatus 28 is placed onto heating element 84 as shown in FIG. 12, and thermal cycling is commenced. Upon completion of the reaction, reaction chamber apparatus 28 is removed from heating element 84, port seal 46 is removed, retaining plate 62 and compression plate 54 are removed by following the corresponding assembly steps in reverse, and finally biochip 20 is removed.

Although the detailed description and operational description previously recited contain many specific details, these should not be construed as limitations on the scope of the invention, but rather as an exemplification of one preferred embodiment thereof. Those with skill in the art will recognize the generality of the exemplified chamber, and the capacity for the recited components as disclosed herein to be varied for any particular purpose or reaction. For example, reaction chamber apparatus 28 could be configured to accommodate a multitude of different configurations of biochip 20, or apparatus 28 could be configured to accommodate a biochip 20 comprising two microarrays each having forty biologically reactive sites in one direction and one hundred in a direction normal to the first direction. The size of reaction chamber apparatus 28 could be scaled to accommodate a substrate up to 310 millimeters wide, 310 millimeters long, and 3 millimeters thick. A high-throughput embodiment of reaction chamber apparatus 28 that can accommodate a plurality of biochips 20 is also possible.

The apparatus could be configured for automatic loading of reaction chamber 30 by integrating an automated fluid pumping system to interface to each fluid port 38 and 39. Such a pumping system would allow introduction of a plurality of fluids into each reaction chamber 30, and agitation and pressurization of fluids in each reaction chamber 30.

Alternative means for creating a sealed reaction chamber around each microarray 24 on substrate surface 22 of biochip 20 also exist. For example, well structures 34, O-rings 48, and O-ring grooves 36 could be replaced with a single shaped gasket member made from a biologically compatible sealing material such as silicone rubber. The thickness of the gasket can easily be selected such that when the substrate is clamped against the base plate the resulting gap between the base plate and substrate is most preferably the same as the depth of a well structure. The disposable gasket reduces the complexity of the apparatus by reducing the number of required elements and alleviates the preventive maintenance required for O-rings.

The Examples that follow are illustrative of specific embodiments of the invention and various uses thereof. They are set forth for explanatory purposes only, and are not to be taken as limiting the invention.

EXAMPLE 1

Preparation, Assembly, and Loading of a Microfluidic Reaction Chamber

Six retaining pins of 300 series stainless steel were press-fitted into apertures on a grade 2 commercially pure titanium base plate containing four well structures. A layer of Xylan 8840 black primer (Whitford Worldwide) was applied to the base plate, followed by a layer of Dupont 856-200 Teflon-FEP clear. The base plate and O-rings were soaked in a 1% Alconox Solution for at least 30 minutes, then thoroughly rinsed in distilled, de-ionized water, and dried with compressed nitrogen or air to ensure proper cleaning.

A clean O-ring (Parker Seal Group, O-Ring Division, Part No. 2-015) was pressed completely down into each O-ring groove on the base plate. A soda glass microscope slide containing four 27×27 microarrays of polyacrylamide gel pads was then inserted into the base plate cavity such that the microarrays faced the base plate.

A low-compression silicone sponge rubber compliance layer (McMaster-Carr Supply Co., Part No. 8623K82) was affixed in the cavity of a Teflon® compression plate by application of the adhesive side of the compliance member to the cavity. The retaining pin apertures in the compression plate were then aligned with the retaining pin heads, and the plate was seated on the base plate with the compliance member seated on the microscope slide.

The pin apertures in a 300 series stainless steel retaining plate were aligned with the retaining pin heads, and the retaining plate was compressed towards the base plate such that the heads extended through and above the retaining plate. The retaining plate was then shifted laterally so that the pin necks engaged the notch of the pin aperture, thereby locking the various components of the apparatus together.

The reaction chambers were loaded by inserting a pipet tip 82 (VWR Scientific Products Corporation, Prod. No. 53510-084) into a fluid port until a seal was created between the tip the port. The reaction fluid was slowly introduced into the reaction chamber using a pipettor (Rainin Instrument Company, P-200). When the reaction chamber and the second fluid port were completely filled with fluid, loading was halted. Each reaction chamber was visually inspected for the presence of gas bubbles immediately after loading. If gas bubbles were present over any microarray, the fluid loading process was restarted. The fluid ports were then sealed by applying the pressure-sensitive adhesive side of a piece of aluminum foil tape (Beckman Instruments, Inc., Part No. 270-538620-A) to lower side of the base plate such that: all fluid ports were covered.

EXAMPLE 2

DNA Hybridization and Labeling

Nucleic acid probe molecules immobilized to each site 26 are single-stranded; therefore, nucleic acid target molecules present within the sample fluid introduced to each site must also be single-stranded and contain a region complementary to the oligonucleotide probe molecules for hybridization to occur. Nucleic acids, however, naturally occur as double-stranded molecules. Directly introducing single-stranded target molecules to the single-stranded oligonucleotide probes immobilized to each site can involve several time consuming steps that require costly reagents and reduce the yield of the starting material. An additional complication arises because single-stranded target molecules are typically longer than the immobilized probe molecules, and often have regions complementary to each other along the same target molecule in addition to the region complementary to the immobilized probe molecule, which may result in hybridization of the target molecule to itself. This anomaly is commonly referred to as a hairpin, and may preclude hybridization of the target molecule with a complementary immobilized probe molecule.

Rapid thermal cycling in reaction chamber device alleviates the problem of hairpin formation. During the thermal cycling process, the heating element first increases the temperature of reaction chamber contents to a level just below that required to cause denaturing of any properly hybridized, double-stranded target/probe molecules in the microarray. Improperly hybridized target/probe molecules in the microarray, however, are denatured at this temperature, as are any long double-stranded molecules.

The apparatus described in Example 1 is used to perform nucleic acid amplification assays as follows. As an example, oligonucleotide probe molecules are used having a sequence length corresponding to a denaturing temperature of 60 degrees centigrade. As shown in Table 1, after the apparatus is assembled, loaded and sealed, the heating element first rapidly increases the temperature of the sample fluid within each reaction chamber to 85 degrees centigrade for 2 minutes and 30 seconds, creating conditions sufficient to denature double-stranded target molecules into single-stranded target molecules free from hairpin anomalies. The heating element then rapidly decreases the temperature of the sample fluid within each reaction chamber to 60 degrees centigrade—the calculated melting temperature of the immobilized probe molecules—for 10 minutes. The region of a single-stranded target molecule complementary to an immobilized probe molecule may then hybridize to that immobilized probe molecule before the target molecule has a chance to form a hairpin or hybridize with another complementary single-stranded target molecule.

In addition to target molecules, the sample fluid contains DNA polymerase and a specific type of free nucleotide, for example a fluorescently-labeled terminating nucleotide. After the target molecules have hybridized to the immobilized probe molecules, the DNA polymerase will covalently attach the free nucleotide to the three prime terminal ends of the five prime linked immobilized probe molecules. The polymerase can synthesize, depending on sequence complementarity, a sister molecule to the target molecule by using the immobilized probe molecule as a template. This allows identification of specific nucleotide bases within the nucleic acid sequence.

As shown in Table 1, the heating element again rapidly increases the temperature of the sample fluid within each reaction chamber again to 85 degrees centigrade for 30 seconds, again creating the conditions required for denaturing of all double-stranded target molecules in reaction chamber 30. Heating and cooling steps are repeated many times to repeat the process of covalently attaching free nucleotides to as many immobilized probe molecules as possible. As shown in Table 1, this may take up to 4 hours to complete.

TABLE 1

| Step | Temperature (Degrees centigrade) | Time (min:sec) |
| --- | --- | --- |
| 1 | 85 | 2:30 |
| 2 | 85 | 0:30 |
| 3 | 60 | 10:00 |
| 4 | Go to step 2 and repeat 20 times | N/A |

This process can be used to query polymorphic nucleotides within a given region by using two oligonucleotide probes that are identical with the exception of a polymorphic base at the 3' terminal ends. The free nucleotides present in the sample fluid are fluorescently-labeled terminating nucleotides. When the target molecules hybridize completely with the oligonucleotide probes, the DNA polymerase is able to add exactly one fluorescent base to the probe molecule. The result can be interpreted as a digital "on/off" signal for each probe site.

An example is shown in FIG. 14. In this example, a blood sample from patient A and a blood sample from patient B are contained in the sample fluid. Two oligonucleotide probes having a polymorphic base at the 3' terminal end are used to hybridize the samples. FIG. 14A illustrates complete hybridization of a region of patient A's sample with a probe having adenine as the 3' base. FIG. 14B illustrates complete hybridization of a region of patient B's sample with a probe having guanine as the 3' terminal base. In each of these cases, the complete hybridization of the target with the probe, allows the DNA polymerase in the sample fluid to attach one labeled base to the probe, and the site will be "on." FIG. 14C, however, illustrates an incomplete hybridization due to a base mismatch between the probe and target molecules at the 3' terminal position on the probe, where the probe contains an adenine and the target contains a guanine. In this case, the DNA polymerase will be unable to attach a labeled base to the probe, and the site will be "off."

It should be understood that the foregoing disclosure emphasizes certain specific embodiments of the invention and that all modifications or alternatives equivalent thereto are within the spirit and scope of the invention as set forth in the appended claims.

What we claim is:

1. An apparatus for performing biological reactions on a substrate layer, comprising:
   (a) a substrate having a first surface containing a plurality of biologically reactive sites disposed theron;
   (b) a base plate having a first surface and a second surface, wherein the first surface further comprises a cavity comprising one or a plurality of well structures;
   (c) a sealing member disposed in each well structure, wherein each sealing member defines a reaction chamber between the surface of the substrate layer containing the biologically reactive sites and the first surface of the base plate; and
   (d) a first fluid port and a second fluid port extending from each reaction chamber to the lower surface of the base plate.

2. The apparatus of claim 1 comprising a multiplicity of reaction chambers in which a plurality of independently controlled biological reactions can be performed.

3. The apparatus of claim 1 further comprising:
   (a) a means for delivering fluid to a reaction chamber through the first fluid port, and
   (b) a means for removing fluid from a reaction chamber through the second fluid port.

4. The apparatus of claim 3 wherein the fluid delivery means comprises tubing attached to the first fluid port and the fluid removal means comprises tubing attached to the second fluid port.

5. The apparatus of claim 1 wherein the diameter of the first and second fluid ports will accommodate the outer diameter of a pipet tip.

6. The apparatus of claim 1 further comprising means for pressurizing the contents of the reaction chambers.

7. The apparatus of claim 1 further comprising a groove in the well structure, wherein the sealing member is seated in the groove.

8. The apparatus of claim 1 further comprising a heating element.

9. The apparatus of claim 8 wherein the heating element further comprises a temperature control element that permits rapid alteration of the temperature of the substrate.

10. The apparatus of claim 1 wherein the base plate is made of a thermally conductive material.

11. The apparatus of claim 8 wherein the base plate is made of titanium, copper, aluminum or ceramic.

12. The apparatus of claim 1 wherein the first surface of the base plate is coated with a biologically compatible material.

13. The apparatus of claim 12 wherein the biologically compatible material is fluorinated ethylene propylene, polypropylene, elemental gold, or elemental platinum.

14. The apparatus of claim 12, further comprising a biologically compatible primer layer disposed between the first surface of the base plate and the biologically compatible base plate surface coating.

15. The apparatus of claim 14 wherein the primer layer is a fluoropolymer.

16. The apparatus of claim 1 wherein the sealing member is an O-ring, a gasket, a compressible washer, or a layer of grease.

17. The apparatus of claim 1 wherein the substrate is a microscope slide.

18. A method for performing biological reactions, comprising the steps of:
   (a) loading a substrate having a first surface containing a plurality of biologically reactive sites into the apparatus of claim 1,
   (b) loading a biological fluid sample into each reaction chamber of the apparatus,
   (c) affixing the fluid port seal to the second surface of the base plate,
   (d) heating the apparatus,
   (e) allowing the reaction to proceed to completion,
   (f) removing the fluid port seal,
   (g) removing the fluid samples from the reaction chambers, and
   (h) removing the substrate from the apparatus.

19. An apparatus according to claim 1, further comprising a compression plate seated on the substrate for affixing the substrate to the base plate.

20. The apparatus of claim 19 wherein the compression plate is removably affixed to the first surface of the base plate.

21. The apparatus of claim 19 wherein the base plate has a perimeter and plurality of retaining pins disposed along the perimeter, and wherein the compression plate has a perimeter and a plurality of apertures disposed along the perimeter aligned with the retaining pins on the base plate, and wherein the compression plate is removable affixed to the base plate by positioning the compression plate so that the retaining pins extend through the apertures.

22. The apparatus of claim 19 further comprising a retaining plate removably seated on the compression plate.

23. The apparatus of claim 19 further comprising a compliance layer disposed between the compression plate and the substrate.

24. The apparatus of claim 23 wherein the compliance layer comprises
   (a) a first layer of low-compression material, and
   (b) a second layer of pressure-sensitive adhesive.

25. The apparatus of claim 24 wherein the first layer of low-compression material is silicone sponge rubber, natural sponge rubber, or neoprene sponge rubber.

26. The apparatus of claim 23 wherein the compliance layer further comprises one or more viewing ports extending through the compliance layer at a position that corresponds to the position of each reaction chamber, and wherein the compression plate further comprises one or more viewing ports extending through the compression plate at a position on the plate that corresponds to the position of each reaction chamber and the position of each viewing port in the compliance layer.

27. The apparatus of claim 19 wherein the compression plate further comprises one or more viewing ports extending through the compression plate at a position on the plate that corresponds to the position of each reaction chamber.

28. The apparatus of claim 19 wherein the compression plate is made of fluorinated ethylene propylene, acetal resin, polyurethane, polypropylene, or acrylonitrile-butadiene-styrene.

29. An apparatus according to claim 1, further comprising a fluid port seal for temporarily closing the fluid ports and isolating the reaction chambers.

30. The apparatus of claim 29 wherein the fluid port seal comprises a layer of thermally conductive material and a layer of biologically inert adhesive.

31. A method for performing biological reactions, comprising the steps of:
   (a) loading a substrate having a first surface containing a plurality of biologically reactive sites into the apparatus of claim 1,
   (b) loading a biological fluid sample into at least one reaction chamber of the apparatus,
   (c) affixing the fluid port seal to the second surface of the base plate,
   (d) heating the apparatus, and
   (e) allowing the reaction to proceed to completion.

32. A method for performing biological reactions according to claim 31, further comprising loading a first biological fluid sample into a first reaction chamber and a second biological fluid sample into a second reaction chamber.

33. An apparatus for performing biological reactions on a substrate having a first surface containing a plurality of biologically reactive sites attached thereto, comprising: thereon;
   (b) a base plate having a first surface and a second surface, wherein the first surface further comprises a first cavity comprising one or a plurality of well structures and a second cavity, and wherein the substrate is removably seated in the cavity, and wherein the well structures are in direct communication with the first surface of the substrate,
   (c) a groove in each well structure having an inner perimeter and a width,
   (d) a sealing member disposed in the groove in each well structure, wherein each sealing member defines a reaction chamber between the first surface of the substrate layer and the first surface of the base plate,
   (e) a compression plate having a cavity and one or more viewing ports extending through the compression plate and corresponding in position to the reaction chambers, wherein the compression plate is removably seated on the second surface of the substrate for removably affixing the substrate in the cavity of the base plate,
   (f) a compliance layer disposed in the cavity of the compression plate having one or more viewing ports extending through the compliance layer and corresponding in position to the reaction chambers;

(g) a retaining plate removably seated on the compression plate,
(h) a plurality of retaining pins disposed around the perimeter of the base plate which are removably inserted into a corresponding plurality of apertures in the compression layer and a corresponding plurality of apertures in the retaining plate,
(i) a biologically compatible primer layer applied to the base plate and the retaining pins,
(j) a biologically compatible surface coating applied to the primer layer,
(k) a first fluid port and a second fluid port extending from each reaction chamber to the lower surface of the base plate,
(l) a fluid port seal for temporarily closing the fluid ports and isolating the reaction chambers from the environment,
(m) a heating element disposed beneath the base plate, and
(n) a thermal cycling device operatively connected to the heating element.

34. An apparatus for performing biological reactions on a substrate layer, comprising:
(a) a substrate having a first surface containing a plurality of biologically reactive sites disposed thereon and a second surface opposite the first surface,
(b) a base plate having a first surface and a second surface, wherein the first surface further comprises a cavity comprising one or a plurality of well structures,
(c) a compression plate removably seated on the substrate for removably affixing the substrate to base plate,
(d) a sealing member disposed in each well structure, wherein each sealing member defines a reaction chamber between the surface of the substrate layer containing the biologically reactive sites and the first surface of the base plate,
(e) a first fluid port and a second fluid port extending from each reaction chamber to the lower surface of the base plate, and
(f) a fluid port seal for temporarily closing the fluid ports and isolating the reaction chambers from the environment.

35. The apparatus of claim 34 comprising a multiplicity of reaction chambers in which a plurality of independently controlled biological reactions can be performed.

36. The apparatus of claim 34 further comprising:
(a) a means for delivering fluid to a reaction chamber through the first fluid port, and
(b) a means for removing fluid from a reaction chamber through the second fluid port.

37. The apparatus of claim 36 wherein the fluid delivery means comprises tubing attached to the first fluid port and the fluid removal means comprises tubing attached to the second fluid port.

38. The apparatus of claim 34 wherein the diameter of the first and second fluid ports will accommodate the outer diameter of a pipet tip.

39. The apparatus of claim 34 further comprising means for pressurizing the contents of the reaction chambers.

40. The apparatus of claim 34 wherein the first surface of the substrate further comprises an array of 3-dimensional anchoring structures for biological molecules.

41. The apparatus of claim 40 wherein the 3-dimensional anchoring structures are gel-pads.

42. The apparatus of claim 41 wherein the 3-dimensional anchoring structures are polyacrylamide gel-pads.

43. The apparatus of claim 34 wherein the compression plate is removably affixed to the first surface of the base plate.

44. The apparatus of claim 43 wherein the base plate has a perimeter and plurality of retaining pins disposed along the perimeter, and wherein the compression plate has a perimeter and a plurality of apertures disposed along the perimeter aligned with the retaining pins on the base plate, and wherein the compression plate is removable affixed to the base plate by positioning the compression plate so that the retaining pins extend through the apertures.

45. The apparatus of claim 34 further comprising a retaining plate removably seated on the compression plate.

46. The apparatus of claim 34 further comprising a compliance layer disposed between the compression plate and the substrate.

47. The apparatus of claim 46 wherein the compliance layer comprises
(a) a first layer of low-compression material, and
(b) a second layer of pressure-sensitive adhesive.

48. The apparatus of claim 47 wherein the first layer of low-compression material is silicone sponge rubber, natural sponge rubber, or neoprene sponge rubber.

49. The apparatus of claim 34 wherein the compression plate further comprises one or more viewing ports extending through the compression plate at a position on the plate that corresponds to the position of each reaction chamber.

50. The apparatus of claim 46 wherein the compliance layer further comprises one or more viewing ports extending through the compliance layer at a position that corresponds to the position of each reaction chamber, and wherein the compression plate further comprises one or more viewing ports extending through the compression plate at a position on the plate that corresponds to the position of each reaction chamber and the position of each viewing port in the compliance layer.

51. The apparatus of claim 34 further comprising a groove in the well structure, wherein the sealing member is seated in the groove.

52. The apparatus of claim 34 wherein the base plate further comprises a second cavity, and wherein the substrate is removably seated in the second cavity.

53. The apparatus of claim 34 further comprising a heating element.

54. The apparatus of claim 53 wherein the heating element further comprises a temperature control element that permits rapid alteration of the temperature of the substrate.

55. The apparatus of claim 34 wherein the substrate is an integral element of the base plate.

56. The apparatus of claim 34 wherein the base plate is made of a thermally conductive material.

57. The apparatus of claim 56 wherein the base plate is made of titanium, copper, aluminum or ceramic.

58. The apparatus of claim 34 wherein the first surface of the base plate is coated with a biologically compatible material.

59. The apparatus of claim 58 wherein the biologically compatible material is fluorinated ethylene propylene, polypropylene, elemental gold, or elemental platinum.

60. The apparatus of claim 58, further comprising a biologically compatible primer layer disposed between the first surface of the base plate and the biologically compatible base plate surface coating.

61. The apparatus of claim 60 wherein the primer layer is a fluoropolymer.

62. The apparatus of claim 34 wherein the sealing member is an O-ring, a gasket, a compressible washer, or a layer of grease.

63. The apparatus of claim 34 wherein the substrate is a microscope slide.

64. The apparatus of claim 34, wherein the fluid port seal comprises a layer of thermally conductive material and a layer of biologically inert adhesive.

65. The apparatus of claim 34 wherein the compression plate is made of fluorinated ethylene propylene, acetal resin, polyurethane, polypropylene, or acrylonitrile-butadiene-styrene.

66. An apparatus for performing biological reactions on a substrate surface, comprising:
- (a) a substrate having a first surface containing a plurality of biologically reactive sites attached thereto and a second surface opposite the first surface,
- (b) a base plate having a first surface and a second surface, wherein the first surface further comprises a cavity and one or a plurality of well structures, and wherein the substrate is removably seated in the cavity, and wherein the well structures are in direct communication with the first surface of the substrate,
- (c) a groove in each well structure having an inner perimeter and a width,
- (d) a sealing member disposed in the groove in each well structure, wherein each sealing member defines a reaction chamber between the first surface of the substrate layer and the first surface of the base plate,
- (e) a compression plate having a cavity and one or more viewing ports extending through the compression plate and corresponding in position to the reaction chambers, wherein the compression plate is removably seated on the second surface of the substrate for removably affixing the substrate in the cavity of the base plate,
- (f) a compliance layer disposed in the cavity of the compression plate having one or more viewing ports extending through the compliance layer and corresponding in position to the reaction chambers,
- (g) a retaining plate removably seated on the compression plate,
- (h) a plurality of retaining pins disposed around the perimeter of the base plate which are removably inserted into a corresponding plurality of apertures in the compression layer and a corresponding plurality of apertures in the retaining plate,
- (i) a biologically compatible primer layer applied to the base plate and the retaining pins,
- (j) a biologically compatible surface coating applied to the primer layer,
- (k) a first fluid port and a second fluid port extending from each reaction chamber to the lower surface of the base plate,
- (l) a fluid port seal for temporarily closing the fluid ports and isolating the reaction chambers from the environment,
- (m) a heating element disposed beneath the base plate, and
- (n) a thermal cycling device operatively connected to the heating element.

67. A method for performing biological reactions, comprising the steps of:
- (a) loading a biological fluid sample into each reaction chamber of the apparatus of claim 30,
- (b) affixing the fluid port seal to the second surface of the base plate,
- (c) heating the apparatus,
- (d) allowing the reaction to proceed to completion,
- (e) removing the fluid port seal,
- (f) removing the fluid samples from the reaction chambers, and
- (g) removing the substrate from the apparatus.

\* \* \* \* \*